United States Patent [19]
Mayer

[11] Patent Number: 5,616,129
[45] Date of Patent: Apr. 1, 1997

[54] NEEDLELESS INJECTION SITE

[75] Inventor: Bruno Franz P. Mayer, Santa Ana, Calif.

[73] Assignee: NIMA Enterprises, Inc., Brea, Calif.

[21] Appl. No.: 401,854

[22] Filed: Mar. 10, 1995

Related U.S. Application Data

[63] Continuation-in-part of Ser. No. 262,994, Jun. 20, 1994.
[51] Int. Cl.⁶ .......................... A61M 5/00; A61M 5/178
[52] U.S. Cl. .......................... 604/167; 604/256; 604/283; 251/149.1
[58] Field of Search .................... 604/164, 167, 604/256, 283, 415, 905

[56] References Cited

U.S. PATENT DOCUMENTS

| | | | |
|---|---|---|---|
| 4,874,377 | 10/1989 | Newgard et al. | 604/167 |
| 4,917,668 | 4/1990 | Haindl | 604/167 |
| 5,064,416 | 11/1991 | Newgard et al. | 604/167 |
| 5,154,703 | 10/1992 | Bonaldo | 604/244 |
| 5,242,393 | 9/1993 | Brimhall et al. | 604/283 X |
| 5,269,771 | 12/1993 | Thomas et al. | 604/167 X |
| 5,273,533 | 12/1993 | Bonaldo | 604/83 |
| 5,300,034 | 4/1994 | Behnke et al. | 604/167 |
| 5,324,270 | 6/1994 | Kayan et al. | 604/167 |
| 5,360,413 | 11/1994 | Leason et al. | 604/256 X |
| 5,405,331 | 4/1995 | Behnke et al. | 604/167 |
| 5,545,142 | 8/1996 | Stephens et al. | 604/167 |

FOREIGN PATENT DOCUMENTS

| | | |
|---|---|---|
| 0544581 | 11/1992 | France. |
| 3105437 | 10/1982 | Germany. |
| 3105437 | 6/1986 | Germany. |

*Primary Examiner*—Sam Rimell
*Assistant Examiner*—Robert V. Racunas
*Attorney, Agent, or Firm*—Stetina Brunda & Buyan

[57] ABSTRACT

A needleless injection site comprising a housing which defines an interior chamber and a central opening which communicates with the interior chamber. The housing further defines a proximally extending dilating projection portion which is coaxially aligned with the central opening and distally extending adapter portion. The dilator projection and adapter portions define a continuous fluid passage. Disposed within the central opening and the interior chamber is a reseal member which has an elastically openable and closable aperture formed therein. The reseal member normally resides in the first position within the housing wherein the aperture is in a closed configuration. The reseal member is deformable such that the application of distally directed pressure thereto will cause the reseal member to distally advance within the housing to a second position wherein the aperture assumes an open configuration and communicates with the fluid passage. The removal of the distally directed pressure from the reseal member will cause it to resiliently return to the first position wherein the aperture reassumes the closed configuration.

39 Claims, 5 Drawing Sheets

NEEDLELESS INJECTION SITE

FIELD OF THE INVENTION

The present application is a continuation-in-part of U.S. application Ser. No. 08/262,994 entitled NEEDLELESS INJECTION SITE filed Jun. 20, 1994, the disclosure of which is expressly incorporated herein by reference. The present invention relates generally to the medical arts, and more particularly to a needleless injection site for use in relation to intravenous infusions.

BACKGROUND OF THE INVENTION

It is common medical practice to intravenously infuse various fluids into the blood vessels of a patient. Such infusion is typically accomplished by the insertion of a hollow introducer needle into a target blood vessel. The introducer needle is fluidly connected to one end of an elongate, flexible tube, the opposite end of which is fluidly connected to a solution bag. The solution bag itself is typically suspended above the patient so as to allow the fluid to flow downwardly through the tubing and into the patient's blood vessel via the introducer needle which remains operatively positioned therewithin. The fluid tube and solution bag are connected to each other via a metering apparatus which controls the infusion rate of fluid from the bag into the tube.

In many intravenous infusion assemblies, an injection site is fluidly coupled within the tubing intermediate the introducer needle and the solution bag. The injection site typically has a Y-shaped configuration and comprises a tubular main body portion having a tubular side arm portion in fluid communication therewith. The distal end of the side arm portion is fluidly connected to the solution bag via an upper segment of the tubing, with the bottom end of the main body portion being fluidly connected to the introducer needle via a lower segment of the tubing. The top end of the main body portion is itself covered by a diaphragm which is typically fabricated from rubber or a similar resilient material.

The inclusion of the injection site within the tubing allows various medications to be selectively infused into the blood vessel of the patient by the addition thereof to the solution flowing from the solution bag into the blood vessel via the upper tubing segment, injection site, lower tubing segment nd introducer needle. This supplemental infusion is typically accomplished through the utilization of a conventional syringe, the needle of which pierces and is extended through the diaphragm disposed on the top end of the main body portion of the injection site. Subsequent to the expulsion of the medication from within the syringe and into the flowing solution, the needle is retracted out of the main body portion of the injection site, with the aperture created in the diaphragm due to the passage of the needle therethrough being substantially closed upon such retraction due to the resiliency of the diaphragm. As will be recognized, the incorporation of the injection site within the tubing allows various medications to be intravenously administered to the patient through the existing infusion site within the blood vessel, thus eliminating the need to subject the patient to additional needle sticks.

Though providing certain benefits to the patient, the injection sites constructed in accordance with the prior art possess certain deficiencies which detract from their overall utility. As previously explained, the use of such injection sites typically requires that the needle of the conventional syringe be extended through (i.e., puncture) the diaphragm attached to the top end of the main body portion of the injection site. However, the necessity of having to utilize a syringe with a needle to facilitate the introduction of the medication into the solution flow is undesirable due to the risk of inadvertent needle sticks. In recognition of this deficiency, there has also been developed in the prior art needleless injection sites which incorporate a diaphragm adapted to assume open and closed configurations without having a needle inserted thereinto. Through these needleless injection sites eliminate the need of having to puncture the diaphragm with a needle, they also possess certain deficiencies which detract from their overall utility. Foremost of these deficiencies is the difficulty associated with disinfecting the injection site, and in particular the diaphragm thereof, subsequent to medication being infused thereinto. In this respect, after each use of the injection site the diaphragm must be cleaned, with such cleaning typically being accomplished through the application of alcohol or a similar disinfecting substance thereto. However, due to the configuration of the diaphragm, complete and effective disinfection thereof is often difficult to achieve, thus increasing the risk of the introduction of contaminates into the solution stream upon subsequent uses of the injection site.

In an effort to overcome the deficiencies associated with the prior art injection sites, Applicant developed the needleless injection site disclosed in co-pending application Ser. No. 08/262,994 entitled NEEDLELESS INJECTION SITE which is the parent of the present application. The present needleless injection site constitutes an improvement over that disclosed in Ser. No. 08/262,994 in that the same is adapted to accommodate needled introducers as well as non-needled introducers in the event the infusion of medication into the injection site must be accomplished in a short time during an emergency situation through the use of a needled introducer.

SUMMARY OF THE INVENTION

In accordance with the present invention, there is provided a needleless injection site comprising a housing which defines an interior chamber and a central opening which communicates with the interior chamber. Preferably formed on the outer surface of the housing about the central opening thereof are Luer threads. The housing further defines an elongate, proximally extending dilator projection portion which is coaxially aligned with the central opening, and an elongate, distally extending adapter portion. The dilator projection and adapter portions define a continuous fluid passage.

The needleless injection site further comprises a reseal member which is disposed within the central opening and the interior chamber of the housing. The reseal member includes an elastically openable and closable aperture formed therein, and normally resides in the first position within the housing wherein the aperture is in a closed configuration. The dilator projection portion of the housing extends into the reseal member. In the preferred embodiment, the reseal member is deformable such that the application of distally directed pressure thereto will cause the reseal member to distally advance within the housing to a second position wherein the aperture assumes an open configuration and communicates with the fluid passage. The removal of the distally directed pressure from the reseal member causes it to resiliently return to the first position wherein the aperture reassumes the closed configuration.

The reseal member comprises an elongate, resilient body defining a distal end, a proximal end having inner and outer surfaces, and an aperture extending between the inner and outer surfaces of the proximal end. Partially encapsulated within the body is a radial leaf spring defining a base portion and a plurality of leaf portions. The leaf portions are adapted to apply a radially inward biasing force to the proximal end of the body which maintains the aperture in the closed configuration when no distally directed pressure is applied to the outer surface of the proximal end. The body and radial leaf spring define a bore which extends longitudinally from the distal end of the body to the inner surface of the proximal end. The dilator projection portion of the housing is received into the bore, with the application of distally directed pressure to the outer surface of the proximal end causing the radial leaf spring to be distally advanced over the dilator projection portion. The resultant outward flexion of the leaf portions facilitates the radial expansion of the aperture to the open configuration. Conversely, the removal of the distally directed pressure from the outer surface causes the radial leaf spring to be proximally withdrawn from over the dilator projection portion, thus facilitating the return of the aperture to the closed configuration. The body portion of the reseal member is preferably fabricated from silicone and comprises a generally frusto-conical proximal portion defining the proximal end and a generally cylindrical distal portion defining the distal end. Formed between the proximal and distal portions is a beveled shoulder. The diameter of the distal portion preferably exceeds the maximum diameter of the proximal portion.

In the preferred embodiment, the body of the reseal member includes a lip which is formed about and extends radially outward from the proximal end thereof, and has a diameter which slightly exceeds the diameter of the central opening of the housing. The outer surface of the proximal end of the body is preferably arcuately contoured, with the inner surface of the proximal end having a generally semi-spherical configuration. The aperture extends axially between the arcuately outer surface and the apex of the semi-spherical inner surface. The inner surface of the proximal end may further include a duck-bill style check valve formed at the apex thereof, with the aperture extending through the check valve. When the dilator projection portion is fully received into the bore of the reseal member, both the shoulder and the distal end of the body are abutted against the housing in a manner wherein a slight compression force is applied to the distal portion. The body further defines an annular flange which is disposed within the bore of the reseal member and abutted against the dilator projection portion when the same is extended into the bore.

In the needleless injection site, the adapter portion of the housing may comprise an elongate spike having a tapered outer surface and a beveled distal tip. Slidably extensible and frictionally maintainable on the spike is a tubular adapter sleeve which has a tapered outer surface and a tapered bore extending longitudinally therethrough. The tapered bore is complimentary to the outer surface of the spike for facilitating the frictional retention of the adapter sleeve thereon. The spike further includes an elongate rib formed on the outer surface thereof, with the bore of the adapter sleeve defining at least one elongate slot therewithin which is sized and configured to receive the rib when the adapter member is slidably advanced over the spike. The receipt of the rib into the slot is operable to prevent the rotation of the adapter sleeve upon the spike.

In the needleless injection site, the housing may further define a distal lock region for facilitating the connection of the housing to an annular, externally threaded surface. The lock region may define a plurality of Luer thread pitch barbs therewithin. Rather than comprising a spike, the adapter portion of the housing may alternatively define a tapered outer surface with a blunt distal tip, with the distal lock region of the housing circumventing the adapter portion and comprising an internally threaded lock member which is rotatably connected to the adapter portion.

In a first embodiment of the present invention, the housing comprises an upper section defining the central opening and a lower section attached to the upper section, with the upper and lower sections defining the interior chamber when attached to each other. In addition to the upper and lower sections, the housing constructed in accordance with the first embodiment comprises an adapter member which includes a flange portion having the dilator projection portion extending proximally from one side thereof and the adapter portion extending distally from the other side thereof. The flange portion of the adapter member is captured between the upper and lower sections of the housing, with at least a portion of the adapter member residing within the interior chamber of the housing. In the first embodiment, the adapter portion preferably has a tapered outer surface and a beveled distal tip, with the lower section of the housing defining the distal lock region for facilitating the connection of the housing to an annular, externally threaded surface.

In a second embodiment of the present invention, the housing comprises an upper section which defines the central opening and a lower section which is attached to the upper section and defines the dilator projection portion and the adapter portion. The upper and lower sections define the interior chamber when attached to each other. In the second embodiment, the adapter portion of the lower section may comprise a spike having a tapered outer surface and a beveled distal tip. Alternatively, the adapter portion may have a tapered outer surface, with the lower section further defining the distal lock region which circumvents the adapter portion for facilitating the connection of the housing to an annular, externally threaded surface.

Further in accordance with the present invention, there is provided a method of fabricating a reseal member comprising the step of advancing a radial leaf spring having a base portion and a plurality of leaf portions over a core which is sized to cause the leaf portions be flexed outwardly when the radial leaf spring is advanced thereover. The preferred method further comprises the steps of molding a body about the radial leaf spring and core in a manner wherein the radial leaf spring is partially encapsulated by the body, and removing the core from within the radial leaf spring and body. The molded body defines a distal end, a proximal end having inner and outer surfaces, and an aperture extending through the proximal end between the inner and outer surfaces thereof. The removal of the core from within the radial leaf spring and body facilitates the formation of a bore which extends longitudinally from the distal end to the inner surface of the proximal end. Such removal also allows the leaf portions of the radial leaf spring to return to an unflexed orientation which results in the application of a radially inward biasing force to the proximal end for maintaining the aperture in a closed configuration.

BRIEF DESCRIPTION OF THE DRAWINGS

These, as well as other features of the present invention, will become more apparent upon reference to the drawings wherein.

DETAILED DESCRIPTION OF THE PREFERRED EMBODIMENTS

Figure 1:
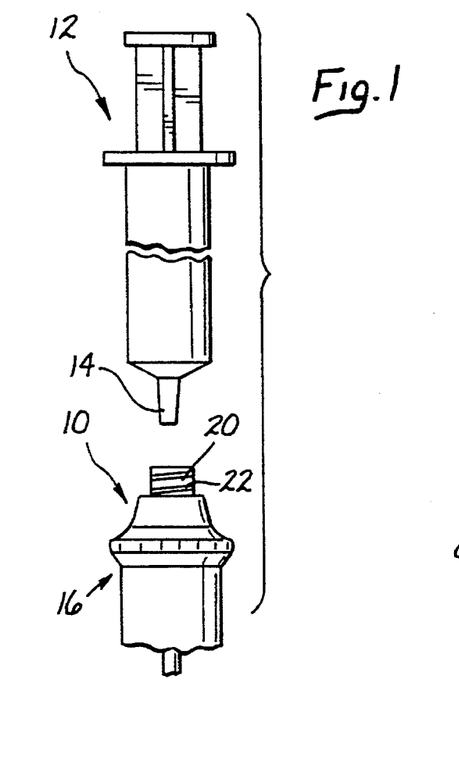
FIG. 1 is a side elevational view of a needleless injection site constructed in accordance with a first embodiment of the present invention, further illustrating an introducer device which may be used in conjunction therewith.
Figure 2:
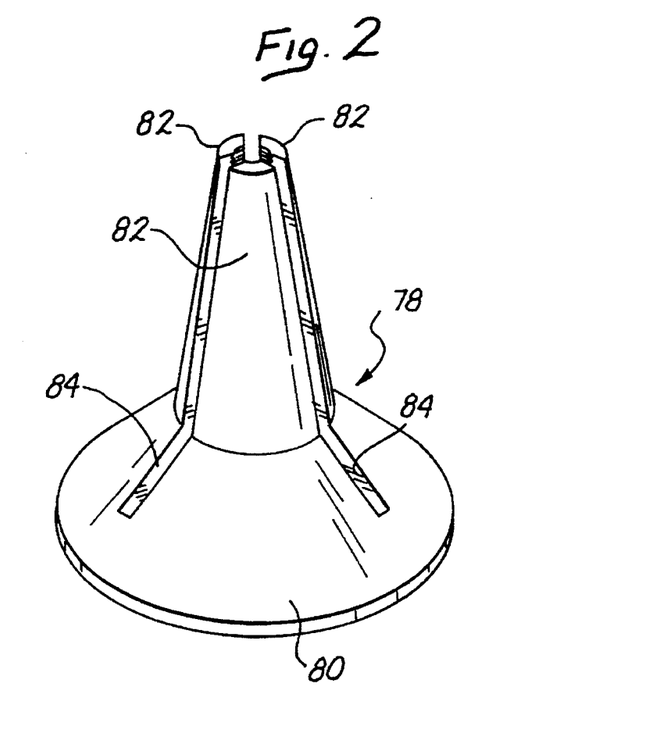
FIG. 2 is a top perspective view of a radial leaf spring incorporated into a reseal member of the needleless injection site shown in FIG. 1.
Figure 3:
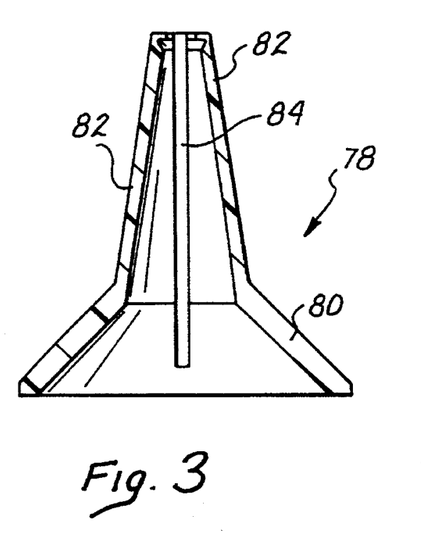
FIG. 3 is a side elevational view of the radial leaf spring shown in FIG. 2.

Referring now to the drawings wherein the showings are for purposes of illustrating preferred embodiments of the present invention only, and not for purposes of limiting the same, FIG. 1 illustrates a needleless injection site 10 constructed in accordance with a first embodiment of the present invention. As further seen in FIG. 1, medications are typically introduced into the injection site 10 via a needleless introducer device 12 such as a syringe which includes a reduced diameter tip 14.

Figure 9:
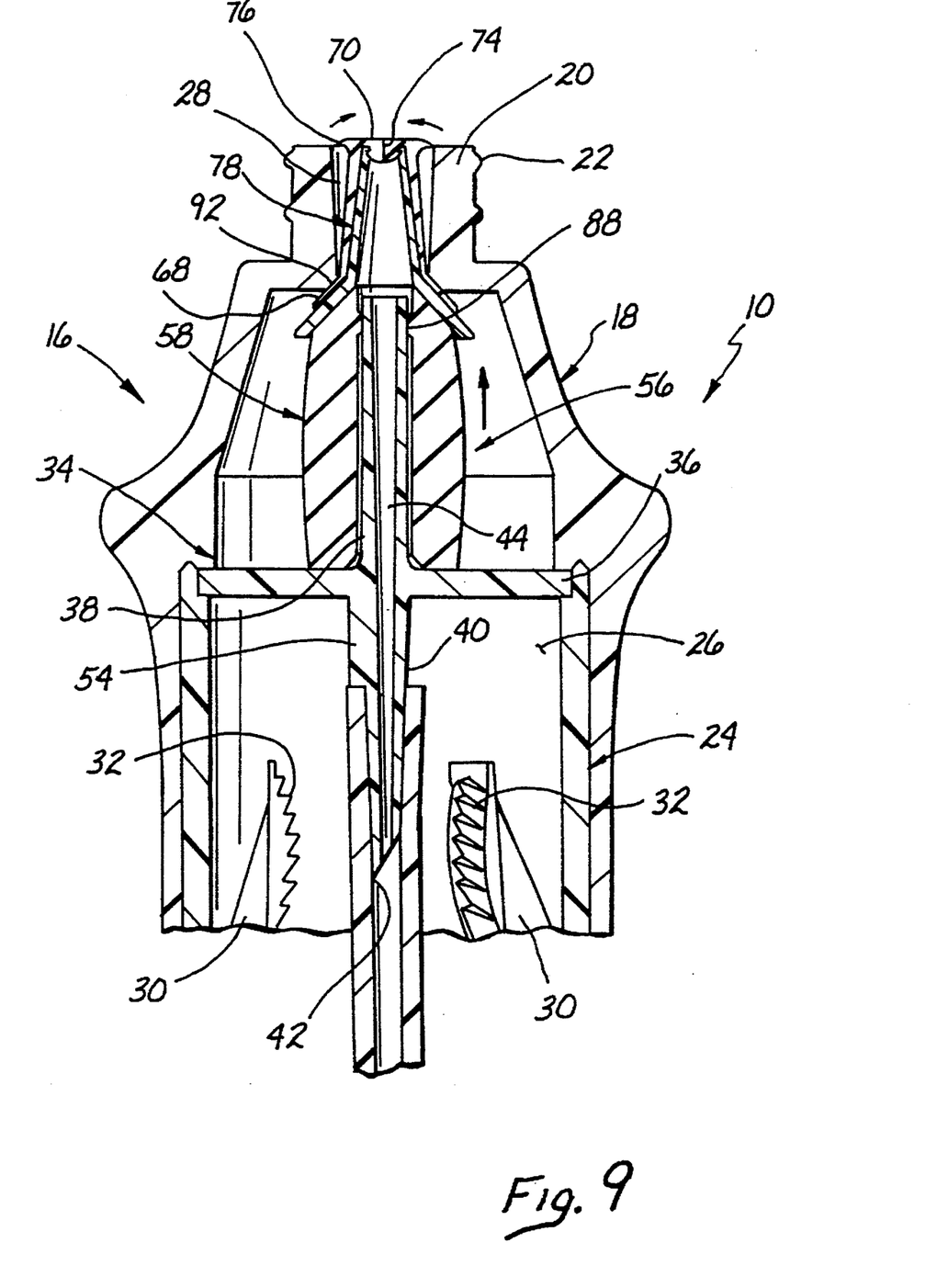
FIG. 9 is a cross-sectional view of the needleless injection site shown in FIG. 1, illustrating the reseal member thereof in a first, closed position.
Figures 10, 10A:
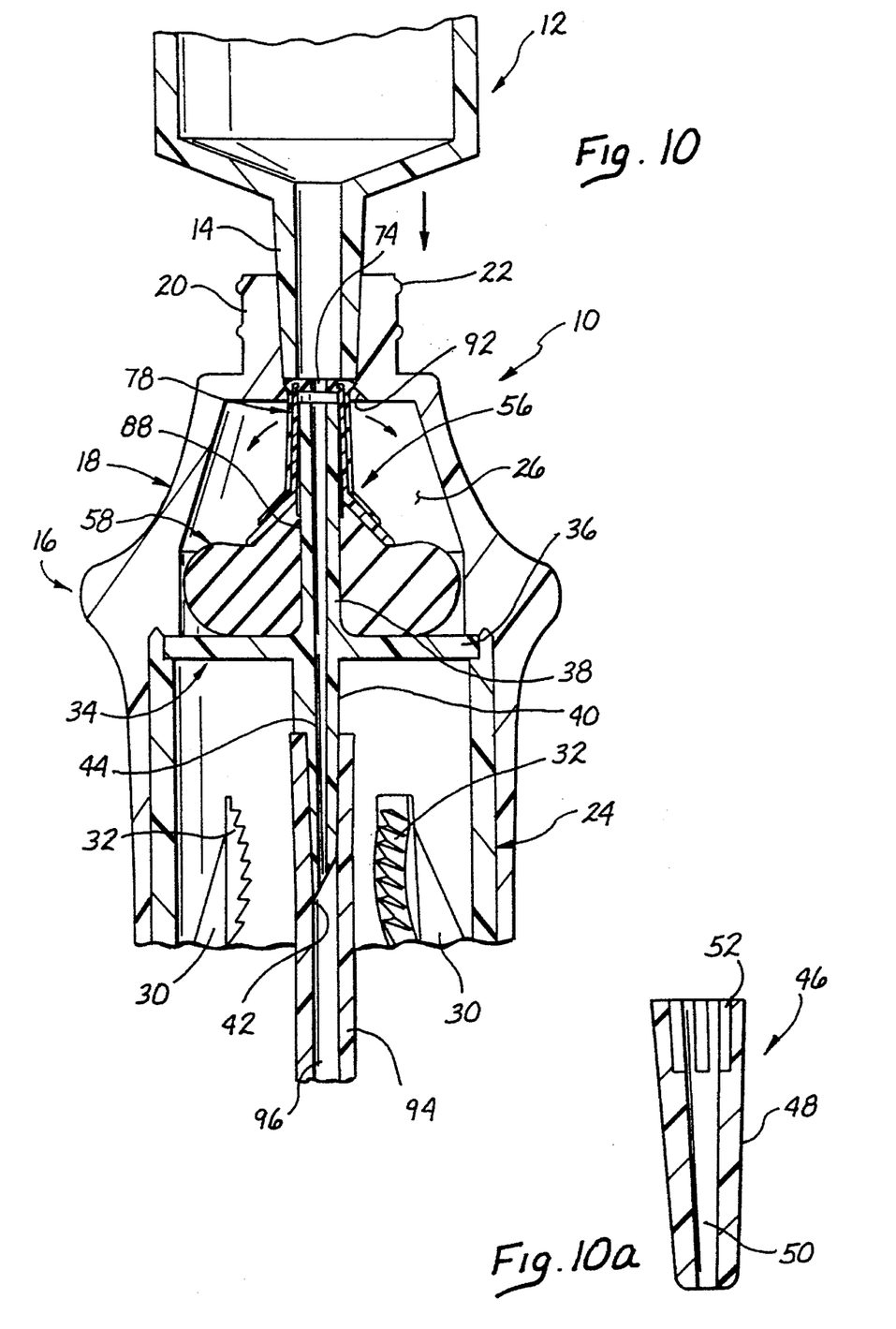
FIG. 10 is a cross-sectional view of the needleless injection site shown in FIG. 1, illustrating the reseal member thereof as deformed into a second, open position.
FIG. 10a is a cross-sectional view of an adapter sleeve which may be used with the needleless injection site shown in FIGS. 1, 9 and 10.

Referring now to FIGS. 9 and 10, the injection site 10 comprises a hollow housing 16. The housing 16 itself comprises an upper section 18 which defines a reduced diameter proximal portion 20 having Luer threads 22 formed on the outer surface thereof. In addition to the upper section 18, the housing 16 comprises a sleeve-like lower section 24 which is insertible into and attachable to the upper section 18. The upper and lower sections 18, 24, when attached to each other, define an interior chamber 26 of the housing 16, with the proximal half of the interior chamber being defined by the upper section 18, and the distal half of the interior chamber 26 being defined by the lower section 24. The proximal portion 20 of the upper section 18 defines a tapered central opening 28 which communicates with the interior chamber 26, and in particular the proximal half thereof. Disposed about the distal rim of the lower section 24 in equidistantly spaced intervals are a plurality of locking tabs 30, each of which include Luer thread pitch barbs 32 formed on the inner surfaces thereof. The locking tabs 30 are formed in a manner wherein the pitch barbs 32 are oriented radially inward from and extend in generally parallel relation to the inner surface of the lower section 24. The use of the locking tabs 30 and associated pitch barbs 32 will be discussed in more detail below.

In addition to the upper and lower sections 18, 24, the housing 16 comprises an adapter member 34 which includes a central, circularly configured flange portion 36. Extending proximally from the flange portion 36 is an elongate dilator projection portion 38 which is coaxially aligned with the central opening 28 of the upper section 18. Extending distally from the flange portion 36 is an elongate adapter portion 40 which is itself coaxially aligned with the dilator projection portion 38. The adapter portion 40 has a tapered outer surface and includes a beveled distal end which defines a piercing tip 42. The dilator projection and adapter portions 38, 40 define a continuous fluid passage 44. In the preferred embodiment, the adapter member 34 is attached to the remainder of the housing 16 via the rigid capture of the peripheral region of the flange portion 36 between the upper and lower sections 18, 24.

Referring now to FIGS. 9, 10 and 10a, the housing 16 may further comprise a tubular adapter sleeve 46 which is selectively attachable to the adapter portion 40 of the adapter member 34. The adapter sleeve 46 has a tapered outer surface 48 and includes a tapered bore 50 extending longitudinally therethrough which is complimentary to the tapered outer surface of the adapter portion 40. Disposed within the side wall of the bore 50 are a plurality of equidistantly spaced slots 52 which extend longitudinally from the end of the adapter sleeve 46 of greater diameter to a depth which is approximately one-fourth the total length of the adapter sleeve 46. In attaching the adapter sleeve 46 to the remainder of the housing 16, the same is slidably advanced over the adapter portion 40. Since the outer surface of the adapter portion 40 and the bore 50 of the adapter sleeve 46 have mutually tapered configurations, the adapter sleeve 46 is frictionally maintained on the adapter portion 40 subsequent to being slidably advanced thereover.

Each of the slots 52 of the adapter sleeve 46 is sized and configured to slidably receive an elongate rib 54 which is formed on the outer surface of the adapter portion 40 and extends longitudinally from the flange portion 36 along approximately one-third of the length of the adapter portion 40. The advancement of the adapter sleeve 46 over the adapter portion 40 is terminated when the rib 54 is fully received into a respective slot 52. Advantageously, the receipt of the rib 54 into a respective slot 52 prevents any rotation of the adapter sleeve 46 upon the adapter portion 40. Unlike the distal end of the adapter portion 40, the end of the adapter sleeve 46 opposite that including the slots 52 has a blunt configuration. The use of the adapter sleeve 46 will be discussed in more detail below.

Figures 4, 6, 8:
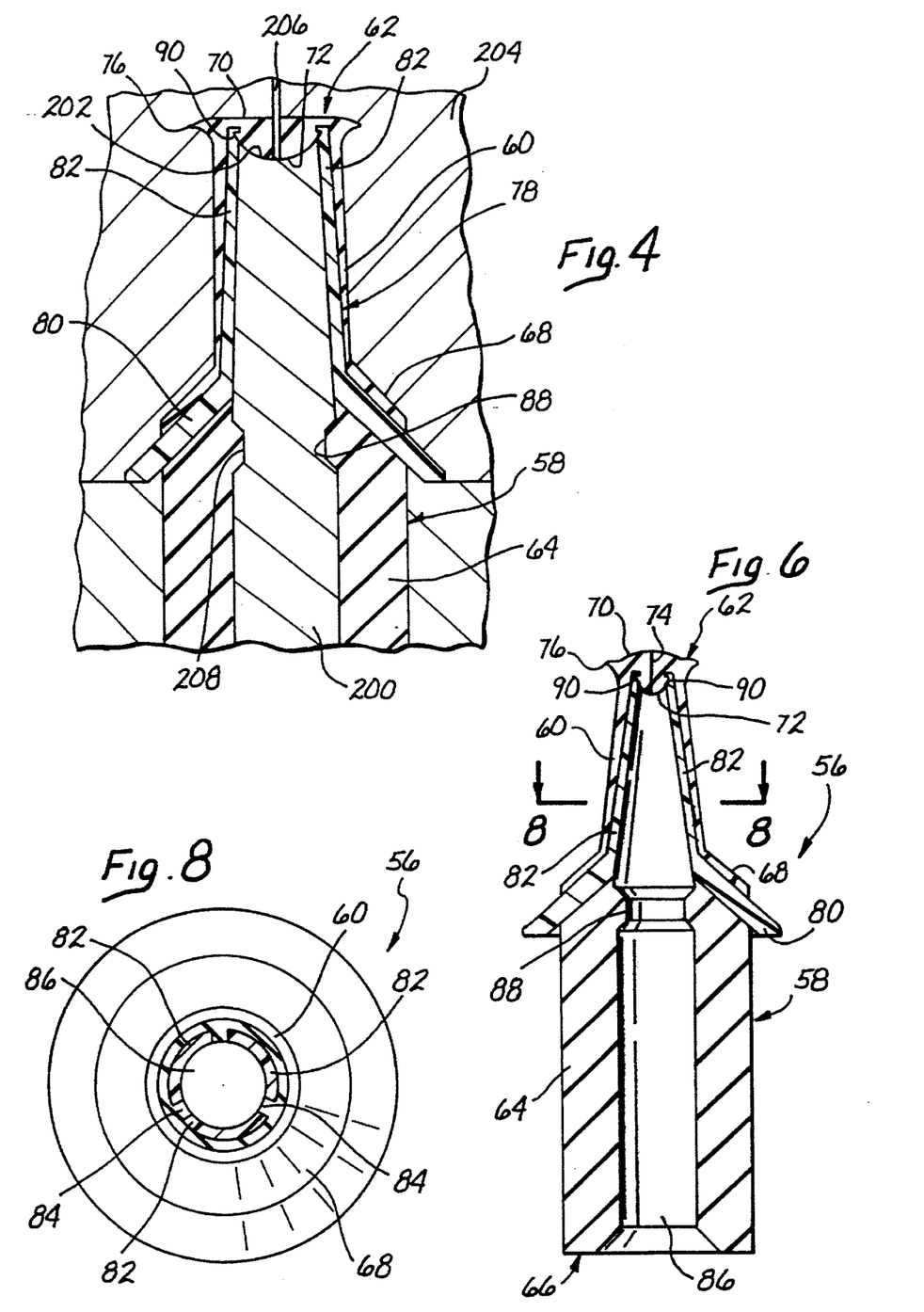
FIG. 4 is a partial cross-sectional view illustrating the preferred manner of forming the reseal member.
FIG. 6 is a cross-sectional view of the reseal member.
FIG. 8 is a cross-sectional view taken along line 8—8 of FIG. 6.

Referring now to FIGS. 6–10, the injection site 10 constructed in accordance with the first embodiment of the present invention further comprises a reseal member 56 which is disposed within the central opening 28 and interior chamber 26 of the housing 16. The reseal member 56 comprises an elongate, resilient body 58 having a generally frusto-conical proximal portion 60 which defines a proximal end 62, and a generally cylindrical distal portion 64 which defines a distal end 66. Formed between the proximal and distal portions 60, 64 is a beveled shoulder 68. The diameter of the distal portion 64 exceeds the maximum diameter of the proximal portion 60. The proximal portion 60 resides within the central opening 28, with the distal portion 64 and shoulder 68 residing within the interior chamber 26. As best seen in FIG. 6, the proximal end 62 of the body 58 defines an arcuately contoured outer surface 70 and a generally semi-spherical inner surface 72. Extending axially through the proximal end 62 from the outer surface 70 to the apex of the inner surface 72 is an aperture 74. Additionally, formed about and extending radially outward from the proximal end 62 is a continuous lip 76 having a diameter which slightly exceeds the diameter of the central opening 28. The body 58 is preferably fabricated from silicone, though the same may alternatively be fabricated from a similar resilient material such as rubber.

Referring now to FIGS. 2, 3 and 6–8, the reseal member 56 further comprises a radial leaf spring 78 which is partially encapsulated within the body 58. The radial leaf spring 78 comprises a beveled base portion 80 having three (3) identically configured, equidistantly spaced leaf portions 82 extending therefrom. The leaf portions 82 are separated from each other by three (3) longitudinally extending slots. 84 which extend into the base portion 80. In the preferred embodiment, the radial leaf spring 78 is partially encapsulated within the body 58 in a manner wherein the proximal portion 60 of the body 58 extends along the outer surfaces of the leaf portions 82, with the inner surface 72 of the proximal end 62 bulging inwardly into the opening defined by the ends of the leaf portions 82. The base portion 80 extends through the distal portion 64 of the body 58, with the peripheral region of the base portion 80 extending radially outward from the outer surface of the distal portion 64 adjacent the shoulder 68.

As best seen in FIG. 6, the reseal member 56 further includes a bore 86 which is defined by the body 58 and radial leaf spring 78, and extends longitudinally from the distal end 66 to the inner surface 72 of the proximal end 62. The body 58 defines an annular flange 88 which is formed within the bore 86 in close proximity to the leaf portions 82 of the radial leaf spring 78. In the preferred embodiment, formed in the inner surfaces of the leaf portions 82 adjacent the ends thereof are grooves 90. The radial leaf spring 78 is encapsulated within the body 58 in a manner wherein portions of the proximal end 62, and in particular the inner surface 72 thereof, are received into the grooves 90. The radial leaf spring 78 is preferably fabricated from polysulfone or polycarbonate, though similar rigid materials with memory may be utilized as an alternative.

Referring now to FIGS. 9 and 10, in the reseal member 56, the aperture 74 extending through the proximal end 62 is elastically openable and closeable. The reseal member 56 normally resides in a first position within the housing 16 (shown in FIG. 9) wherein the aperture 74 is in a closed configuration, and is deformable such that the application of distally directed pressure thereto will cause the reseal member 56 to distally advance within the housing 16 to a second position (shown in FIG. 10) wherein the aperture 74 assumes an open configuration and communicates with the fluid passage 44 of the adapter member 34. Due to the resiliency of the body 58, the removal of the distally directed pressure from the reseal member 56 will cause the same to resiliently return to the first position wherein the aperture 74 reassumes the closed configuration.

When the reseal member 56 is in the first position shown in FIG. 9, the dilator projection portion 38 of the adapter member 34 is fully extended into the bore 86 of the reseal member 56, with the proximal end of the dilator projection portion 38 extending to approximately the leaf portions 82 of the radial leaf spring 78. In this respect, the annular flange 88 formed within the bore 86 is abutted against the outer surface of the dilator projection portion 38 in close proximity to the proximal end thereof. Additionally, the outer surface 70 of the proximal end 62 is substantially flush with the rim of the proximal portion 20 of the upper section 18, with the peripheral edge of the lip 76 formed about the proximal end 62 being abutted against the side wall of the central opening 28. Further, the beveled shoulder 68 of the body 58 is abutted against a complimentary beveled ramp 92 which defines the transition between the central opening 28 and interior chamber 26 of the housing 16, with the distal end 66 of the body 58 being abutted against the flange portion 36 of the adapter member 34.

In the preferred embodiment, the distance separating the ramp 92 from the flange portion 36 of the adapter member 34 slightly exceeds the length of the body 58 excluding the proximal portion 60 thereof. As such, when the reseal member 56 is disposed in the first position within the housing 16, the distal portion 64 of the body 56 is slightly compressed between the ramp 92 and flange portion 36, thus applying a pre-load thereto which causes the same to bulge slightly outwardly as shown in FIG. 9. Importantly, when the reseal member 56 is in the first position, the leaf portions 82 of the radial leaf spring 78 apply a radially inward biasing force to the proximal end 62 of the body 58 which maintains the aperture 74 in the closed configuration. The application of the radially inward biasing force is assisted by the abutment of the ramp 92 against the shoulder 68 of the body 58 which also applies a radially inward force to the leaf portions 82.

As best seen in FIG. 10, the application of distally directed pressure to the outer surface 70 of the proximal end 62 by the tip 14 of the introducer device 12 causes the radial leaf spring 78 to be distally advanced over the dilator projection portion 38. Such advancement removes the shoulder 68 out of its abutting contact with the ramp 92 and facilitates the compression of the distal portion 64 of the body 58, thus causing the same to bulge outwardly. Importantly, the camming action of the dilator projection portion 38 against the inner surfaces of the leaf portions 82 causes the same to be flexed outwardly, thus facilitating the radial expansion of the aperture 74 to the open configuration. Due to the resiliency of the body 58, and in particular the distal portion 64 thereof, the removal of the distally pressure from the outer surface 70 of the proximal end 62 causes the radial leaf spring 78 to be proximally withdrawn from over the dilator projection portion 38, thus facilitating the return of the reseal member 56 to the first position and resultant collapse of the aperture 74 to the closed configuration.

When the reseal member 56 is moved to the second position and the aperture 74 opened as shown in FIG. 10, a continuous flow path is created between the introducer device 12 and fluid passage 44 of the adapter member 34. Importantly, medication expelled from the introducer device 12 is prevented from leaking into the interior chamber 26 of the housing 16 by the abutment of the tip 14 of the introducer device 10 against the outer surface 70 of the proximal end 62, as well as the sliding seal created by the abutment of the lip 76 against the side wall of the central opening 28. Additionally, any fluid passing through the aperture 74 which does not enter the fluid passage 44 is prevented from flowing into the interior chamber 26 by the sliding seal created by the abutment of the annual flange 88 against the outer surface of the dilator projection portion 38.

As shown in FIGS. 9 and 10, the injection site 10 is coupled to a standard tubular fluid line 94 defining a hollow lumen 96. The connection of the injection site 10 to the fluid line 94 is accomplished by the slidable advancement of the adapter portion 40 into the lumen 96, with the adapter portion 40 being frictionally maintained therewithin. As such, upon the movement of the reseal member 56 to the second position, medication may be passed from the introducer device 12 into the lumen 96 of the fluid line 94 via the flow path defined by the open aperture 74 and fluid passage 44 of the adapter member 34. Though the injection site 10 is shown in FIGS. 9 and 10 as being connected to the fluid line 94, it will be recognized that the same may also be selectively coupled to other infusion components such as a Luer connector, Y-injection site or bottle through the utilization of the locking tabs 30. Typically, when the injection site 10 is to be connected to a Luer connector, the adapter sleeve 46 will be attached to the adapter portion 40 in the aforementioned manner.

Due to the configuration of the reseal member 56, in an emergency situation medication may be passed into the fluid passage 44 via a needled introducer device rather than through the non-needled introducer device 12 previously described. In this respect, when a needled introducer device is utilized, the reseal member 56 will not be moved to the second position to facilitate the opening of the aperture 74. Rather, the needle of the needled introducer device is simply forced through the closed aperture 74 and into the fluid passage 44 of the dilator projection portion 38. Importantly, even if the tip of the needle is not extended into the fluid passage 44, any medication dispensed therefrom will still flow into the fluid passage 44, and will be prevented from flowing into the interior chamber 26 by the seal created by the abutment of the flange 88 against the outer surface of the dilator projection portion 38. Advantageously, due to the ends of the leaf portions 82 being embedded in the inner surface 72 of the proximal end 62 as a result of the same being partially received in the grooves 90, the plug created by the protrusion of the inner surface 72 into the opening defined by the leaf portions 82 is maintained during the removal of the needled introducer device from within the aperture 74.

Figures 7, 11:
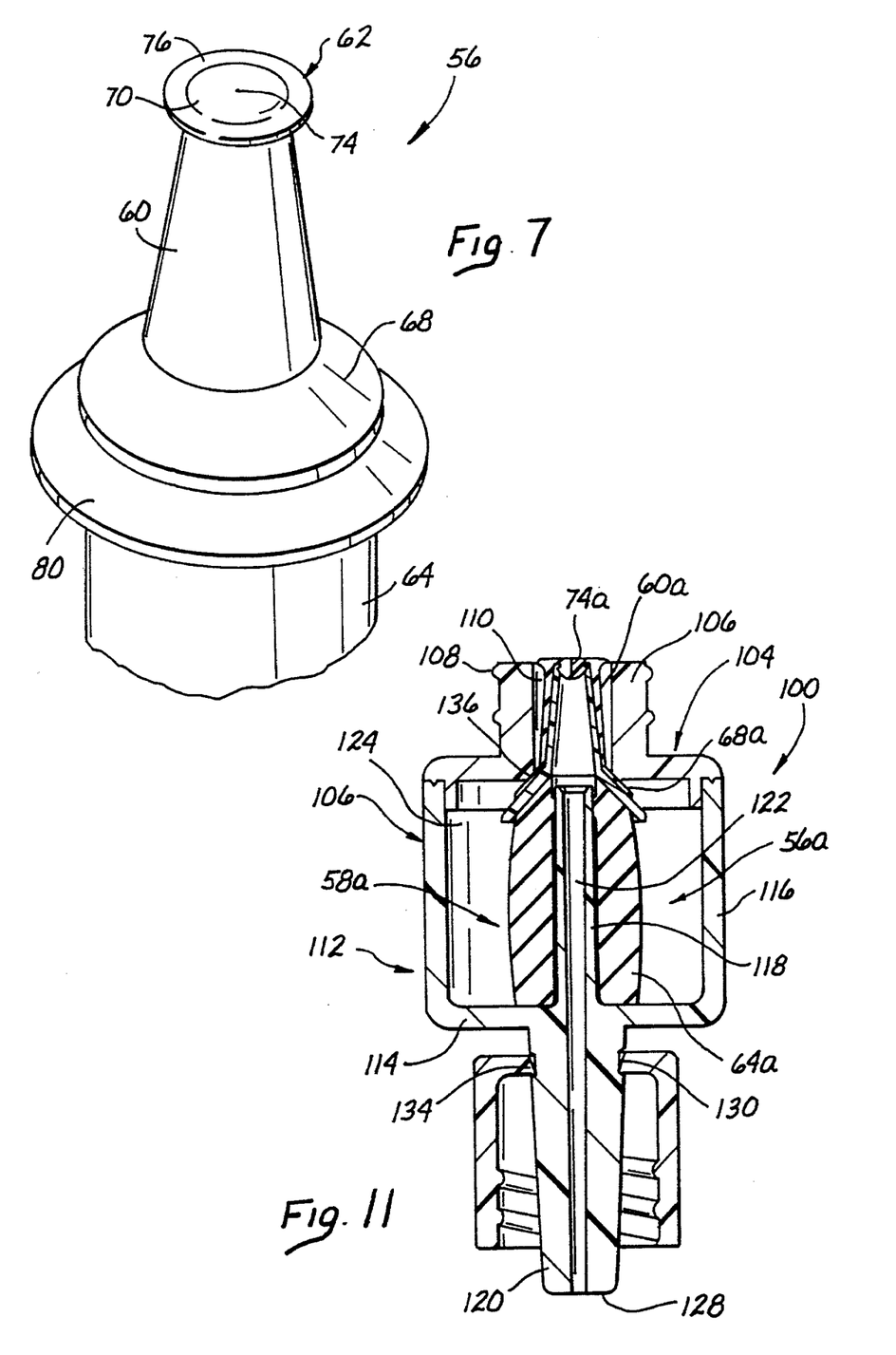
FIG. 7 is a partial top perspective view of the reseal member.
FIG. 11 is a cross-sectional view of a needleless injection site constructed in accordance with a second embodiment of the present invention.

Referring now to FIG. 11, there is shown a needleless injection site 100 constructed in accordance with a second embodiment of the present invention. The injection site 100 comprises a housing 102 which itself comprises an upper section 104 having a reduced diameter proximal portion 106. The proximal portion 106 includes Luer threads 108 formed on the outer surface thereof, and defines a tapered central opening 110. In addition to the upper section 104, the housing 102 comprises a lower section 112 which is attached to the upper section 104 and includes a bottom wall 114 and a continuous side wall 116. Extending proximally from the bottom wall 114 is a dilator projection portion 118 which is coaxially aligned with the central opening 110. Extending distally from the bottom wall 114 is an adapter portion 120 which is itself coaxially aligned with the dilator projection portion 118. The dilator projection and adapter portions 118, 120 define a continuous fluid passage 122. The upper and lower sections 104, 112, when attached to each other, define an interior chamber 124 of the housing 102. In this respect, the central opening 110 of the upper section 104 communicates with the interior chamber 124.

In the second embodiment, the adapter portion 120 defines a tapered outer surface and a blunt distal end 128. Formed in the outer surface of the adapter portion 120 in close proximity to the bottom wall 114 is a continuous groove 130. Rotatably connected to the adapter portion 120 is an internally threaded lock member 132 which includes a radially inwardly extending flange portion 134. The rotatable connection of the lock member 132 to the adapter portion 120 is facilitated by the receipt of the flange portion 134 into the groove 130.

The injection site 100 further comprises a reseal member 56a which is identical to the previously described reseal member 56 and is disposed within the interior chamber 124 and central opening 110 of the housing 102. The proximal portion 60a of the reseal member 56a is disposed within the central opening 110, with the distal portion 64a being slightly compressed between an annular ramp 136 defining the transition between the central opening 110 and interior chamber 124, and the bottom wall 114 of the lower section 112. In this respect, the shoulder 68a of the body 58a is abutted against the ramp 136, with the distal end of the body 58a being abutted against the bottom wall 114. As in the injection site 10, the distance separating the ramp 136 from the bottom wall 114 slightly exceeds the length of the body 58a excluding the proximal portion 60a thereof, thus facilitating the compression of the distal portion 64a.

The reseal member 56a is shown in FIG. 11 in the first position wherein the aperture 74a of the body 58a is in the closed configuration. The movement of the reseal member 56a to the second position wherein the aperture 74a assumes the open configuration occurs in the same manner as previously described in relation to the injection site 10. Additionally, a needled introducer may be used in conjunction with the injection site 100 by extending the needle through the closed aperture 74a and into the fluid passage 122. The injection site 100 is adapted for use with a Luer connector, with the internally threaded lock member 132 being threadably engageable to the Luer threads of the Luer connector subsequent to the insertion of the adapter portion 120 thereinto. As will be recognized, the adapter portion 120 has an external configuration which is substantially identical to that of the adapter portion 40 of the previously described injection site 10 subsequent to the slidable advancement of the adapter sleeve 46 thereover.

As previously explained, the housings 16, 102 of the injection sites 10, 100 are adapted to be connectible to infusion components such as a Luer connector, a Y-injection site, a standard tubular fluid line, and a bottle. It will be recognized that other injection sites may be fabricated which comprise the reseal member 56, 56a incorporated into a differently configured housing without departing from the spirit and scope of the invention. In this respect, any housing with which the reseal member 56, 56a is utilized need only be configured so that the reseal member 56, 56a is movable from the first to the second positions to create a continuous fluid passage from the introducer device into the infusion component in the previously described manner.

Referring now to FIG. 4, the preferred method of fabricating the reseal member 56 (and hence the reseal member 56a) comprises the step of advancing the radial leaf spring 78 over a solid core 200 which is sized to cause the leaf portions 82 of the radial leaf spring 78 to be flexed outwardly when the radial leaf spring 78 is advanced over the core 200. Formed in the proximal end of the core 200 is an arcuately contoured, generally semi-circular recess 202. Importantly, the radial leaf spring 78 is advanced over the core 200 to a position whereat the grooves 90 formed in the ends of the leaf portions 82 are disposed immediately adjacent the recess 202. The core 200 having the radial leaf spring 78 positioned thereon is then placed into a mold 204 having a cavity which approximates the shape of the body 58. The mold 204 includes a pin 206 which extends perpendicularly through the cavity into contact with the apex of the recess 202 formed in the proximal end of the core 200.

Subsequent to the placement of the core 200 and radial leaf spring 78 into the mold cavity of the mold 204, the body 58 is injection molded about the radial leaf spring 78 and core 200 in a manner wherein the radial leaf spring 78 is partially encapsulated by the body 58 in the previously described manner. Importantly, the silicone from which the body 58 is preferably formed flows into the slots 84 of the radial leaf spring 78 during the molding process, thus facilitating the positive engagement between the proximal portion 60 and leaf portions 82. The core 200 further includes a continuous channel 208 circumventing the outer surface thereof which facilitates the formation of the flange 88 within the body 58. Additionally, the flow of the silicone into the recess 202 of the core 200 during the molding process facilitates the formation of the inner surface 72 of the proximal end 62 with the semi-spherical configuration, with the flow of the silicone into the grooves 90 facilitating the positive engagement between the proximal end 62 and leaf portions 82 for the reasons previously described. Upon the solidification of the body 58, the same (along with the integral radial leaf spring 78) is removed from within the mold 204. As will be recognized, the withdrawal of pin 206 of the mold 204 from within the proximal end 62 of the body 58 facilitates the formation of the aperture 74. Subsequent to the removal of the body 58 and integral radial leaf spring 78 from within the mold 204, the core 200 is removed from therewithin, thus facilitating the formation of the bore 86.

Figure 5:
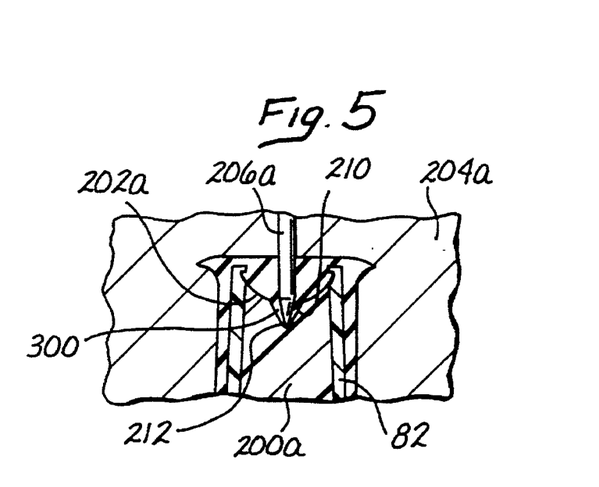
FIG. 5 is a partial cross-sectional view illustrating an alternative method of forming a portion of the reseal member.

Referring now to FIG. 5, the reseal member 56 may alternatively be formed through the utilization of a core 200a which is identical to the previously described core 200, but further includes a conically shaped notch 210 formed in the apex of the semi-spherical recess 202a disposed in the proximal end thereof. When the core 200a is utilized, the pin 206a of the mold 204a is provided with a pin point 212 which extends to the apex of the notch 210. Importantly, the body formed through the utilization of the core 200a and accompanying pin 206a will include a duckbill style check valve 300 which is formed at the apex of the semi-spherical inner surface thereof. The check valve 300 may be provided with the reseal member 56 for purposes of preventing any medication from back flowing into the introducer device 12. It will be recognized that the check valve 300 may also be formed with alternative configurations.

Additional modifications and improvements of the present invention may also be apparent to those skilled in the art. Thus, the particular combination of parts described and illustrated herein is intended to represent only certain embodiments of the present invention, and is not intended to serve as limitations of alternative devices within the spirit and scope of the invention.

What is claimed is:

1. A needleless injection site, comprising:

a housing defining:

an interior chamber;

a central opening which communicates with the interior chamber;

an elongate, proximally extending dilator projection portion which is coaxially aligned with said central opening; and an elongate, distally extending adapter portion, said dilator projection and adapter portions defining a continuous fluid passage;

a reseal member disposed within said central opening and said interior chamber, said reseal member having an elastically openable and closable aperture formed therein and normally residing in a first position within the housing wherein the aperture is in a closed configuration, the dilator projection portion of the housing extending into the reseal member;

said reseal member being deformable such that the application of distally directed pressure thereto will cause the reseal member to distally advance within the housing to a second position wherein the aperture assumes an open configuration and communicates with the fluid passage, and the removal of the distally directed pressure therefrom will cause the reseal member to resiliently return to the first position wherein the aperture reassumes the closed configuration.

2. The injection site of claim 1 wherein said reseal member comprises:

an elongate, resilient body having a distal end and a proximal end which defines inner and outer surfaces, said aperture extending through the proximal end between the inner and outer surfaces thereof;

a radial leaf spring partially encapsulated within said body and adapted to apply a radially inward biasing force to the proximal end which maintains the aperture in the closed configuration when no distally directed pressure is applied to the outer surface of the proximal end; and a bore extending longitudinally from the distal end of the body to the inner surface of the proximal end, said bore being defined by said body and said radial, leaf spring;

said dilator projection portion being received into the bore, with the application of distally directed pressure to the outer surface of the proximal end causing the radial leaf spring to be distally advanced over the dilator projection portion which facilitates the radial expansion of the aperture to the open configuration, and the removal of the distally directed pressure from the outer surface causing the radial leaf spring to be proximally withdrawn from over the dilator projection portion which facilitates the return of the aperture to the closed configuration.

3. The injection site of claim 2 wherein said body comprises:

a generally frusto-conical proximal portion defining said proximal end;

a generally cylindrical distal portion defining said distal end; and a beveled shoulder formed between the proximal and distal portions;

the diameter of said distal portion exceeding the maximum diameter of said proximal portion.

4. The injection site of claim 3 wherein the distal end and the beveled shoulder of the body are abutted against the housing and the distal portion of the body is compressed when the dilator projection portion is fully extended into the bore.

5. The injection site of claim 2 wherein said body includes a lip formed about and extending radially outward from the proximal end thereof, said lip having a diameter slightly exceeding the diameter of the central opening.

6. The injection site of claim 2 wherein said body defines an annular flange disposed within the bore of the reseal member.

7. The injection site of claim 2 wherein said body is fabricated from silicone.

8. The injection site of claim 2 wherein the inner surface of the proximal end has a generally semi-spherical configuration and said aperture extends axially between the outer surface and the apex of the inner surface.

9. The injection site of claim 8 wherein the outer surface of said proximal end is arcuately contoured.

10. The injection site of claim 8 wherein the inner surface of the proximal end includes a check valve formed at the apex thereof, said aperture extending through said check valve.

11. The injection site of claim 10 wherein said check valve comprises a duck-bill style check valve.

12. The injection site of claim 2 wherein said radial leaf spring comprises a base portion and a plurality of leaf portions, said leaf portions applying the radially biasing force to the proximal end of the body which maintains the aperture in the closed configuration.

13. The injection site of claim 1 wherein said housing defines an outer surface having Luer threads formed thereon about the central opening thereof.

14. The injection site of claim 1 wherein the adapter portion of the housing comprises a spike having a beveled distal tip.

15. The injection site of claim 14 wherein the spike has a tapered outer surface.

16. The injection site of claim 14 wherein said housing further comprises a tubular adapter sleeve slidably extensible over and frictionally maintainable on the spike.

17. The injection site of claim 16 wherein the spike has a tapered outer surface and the adapter sleeve has a tapered bore extending longitudinally therethrough which is complimentary to the outer surface of the spike for facilitating the frictional retention of the adapter sleeve thereon.

18. The injection site of claim 17 wherein the spike includes an elongate rib formed on the outer surface thereof and the bore of the adapter sleeve defines at least one elongate slot therewithin which is sized and configured to receive the rib when the adapter member is slidably advanced over the spike, the receipt of the rib into the slot being operable to prevent the rotation of the adapter sleeve upon the spike.

19. The injection site of claim 17 wherein the adapter sleeve has a tapered outer surface.

20. The injection site of claim 14 wherein said housing further defines a distal lock region for facilitating the connection of the housing to an annular, externally threaded surface.

21. The injection site of claim 20 wherein said lock region defines a plurality of Luer thread pitch barbs therewithin.

22. The injection site of claim 1 wherein said housing further defines a distal lock region circumventing the adapter portion for facilitating the connection of the housing to an annular, externally threaded surface.

23. The injection site of claim 22 wherein the adapter portion of the housing has a tapered outer surface.

24. The injection site of claim 22 wherein said lock region comprises an internally threaded lock member rotatably connected to the adapter portion.

25. The injection site of claim 1 wherein said housing comprises:

an upper section defining said central opening; and a lower section attached to said upper section and defining said dilator projection portion and said adapter portion, said upper and lower sections defining the interior chamber when attached to each other.

26. The injection site of claim 25 wherein the reseal member is abutted against and compressed between the upper and lower sections of the housing when the dilator projection is fully extended thereinto.

27. The injection site of claim 25 wherein said adapter portion comprises a spike having a tapered outer surface and a beveled distal tip.

28. The injection site of claim 25 wherein said adapter portion has a tapered outer surface and said lower section further defines a distal lock region circumventing the adapter portion for facilitating the connection of the housing to an annular, externally threaded surface.

29. The injection site of claim 1 wherein said housing comprises:

an upper section defining said central opening;

a lower section attached to said upper section, said upper and lower sections defining the interior chamber when attached to each other; and an adapter member comprising:
a flange portion;
the dilator projection portion extending proximally from the flange portion; and
the adapter portion extending distally from the flange portion;
said flange portion being captured between the upper and lower sections with at least a portion of the adapter member residing within the interior chamber.

30. The injection site of claim 29 wherein the reseal member is abutted against and compressed between the flange portion of the adapter member and the upper section of the housing when the dilator projection portion is fully extended into the reseal member.

31. The injection site of claim 29 wherein the adapter portion has a tapered outer surface and a beveled distal tip and the lower section of the housing defines a distal lock region for facilitating the connection of the housing to an annular, externally threaded surface.

32. A reseal member for use in a needleless injection site, comprising:

an elongate, resilient body defining a distal end, a proximal end having inner and outer surfaces, and an aperture extending between the inner and outer surfaces of the proximal end; and a radial leaf spring partially encapsulated within said body and defining a base portion and a plurality of leaf portions, said leaf portions applying a radially inward biasing force to the proximal end of the body which maintains the aperture in a closed configuration;

said body and radial leaf spring defining a bore which extends longitudinally from the distal end to the inner surface of the proximal end.

33. The reseal member of claim 32 wherein the inner surface of the proximal end has a generally semi-spherical configuration, said aperture extending axially between the outer surface and the apex of the inner surface.

34. The reseal member of claim 33 wherein the outer surface of the proximal end has an arcuately contoured configuration.

35. The reseal member of claim 33 wherein the inner surface of the proximal end includes a check valve formed at the apex thereof, said aperture extending through said check valve.

36. The reseal member of claim 35 wherein said check valve comprises a duck-bill style check valve.

37. The reseal member of claim 32 wherein said body is fabricated from silicone.

38. The reseal member of claim 32 wherein said body defines an annular flange disposed within the bore.

39. The reseal member of claim 32 wherein said body includes a lip formed about and extending radially outward from the proximal end thereof.

* * * * *

UNITED STATES PATENT AND TRADEMARK OFFICE
Certificate

Patent No. 5,616,129                                                                        Patented: April 1, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Bruno Franz P. Mayer, Santa Ana, Calif.; and Dongchul Dan Hyun.

Signed and Sealed this Eighth Day of September, 1998.

WYNN WOOD COGGINS, *SPE*
Art Unit 3734